US008245423B2

(12) United States Patent  (10) Patent No.: US 8,245,423 B2
Goslee  (45) Date of Patent: Aug. 21, 2012

(54) MEDICAL MANAGER

(76) Inventor: Janet M. Goslee, Columbia, SC (US)

( * ) Notice: Subject to any disclaimer, the term of this patent is extended or adjusted under 35 U.S.C. 154(b) by 166 days.

(21) Appl. No.: 12/757,367

(22) Filed: Apr. 9, 2010

(65) Prior Publication Data

US 2010/0258613 A1 Oct. 14, 2010

Related U.S. Application Data (60) Provisional application No. 61/168,136, filed on Apr. 9, 2009.

(51) Int. Cl.
*G09F 7/12* (2006.01)
(52) U.S. Cl. ............ 40/388; 40/405; 281/15.1; 434/408
(58) Field of Classification Search .................. 40/359, 40/606.07
See application file for complete search history.

(56) References Cited

U.S. PATENT DOCUMENTS

| | | | | |
|---|---|---|---|---|
| 683,632 A * | 10/1901 | Wright | ............... | 281/15.1 |
| 2,096,559 A * | 10/1937 | Riley | ............... | 16/225 |
| 2,610,421 A * | 9/1952 | Horn | ............... | 40/534 |
| 3,008,248 A * | 11/1961 | Steinthal | ............... | 206/472 |
| 3,629,960 A * | 12/1971 | Roush | ............... | 434/429 |
| 3,659,355 A * | 5/1972 | Aubin, Jr. | ............... | 434/408 |
| 3,740,879 A * | 6/1973 | Patterson | ............... | 40/388 |
| 4,010,553 A * | 3/1977 | Bennett | ............... | 434/338 |
| 4,106,230 A * | 8/1978 | Martinez | ............... | 40/773 |
| D278,445 S | 4/1985 | Hartney | ............... | D19/26 |
| 4,687,227 A * | 8/1987 | Kehoe | ............... | 281/45 |
| 4,759,520 A * | 7/1988 | Levine | ............... | 248/174 |
| 4,776,799 A * | 10/1988 | Walsh | ............... | 434/238 |
| 5,007,192 A * | 4/1991 | Hochberg | ............... | 40/661 |
| 5,123,676 A | 6/1992 | Donnelly et al. | ............... | 283/37 |
| 5,127,756 A | 7/1992 | Lumm | ............... | 402/79 |
| D330,115 S | 10/1992 | O'Brien | ............... | D3/56 |
| 5,213,433 A * | 5/1993 | An | ............... | 402/14 |
| D349,733 S * | 8/1994 | Svee | ............... | D20/42 |
| 5,407,230 A * | 4/1995 | Brink et al. | ............... | 281/15.1 |
| D360,578 S | 7/1995 | Dees | ............... | D9/305 |
| 5,433,546 A | 7/1995 | Kershaw | ............... | 402/79 |
| 5,492,268 A | 2/1996 | Biddle et al. | ............... | 229/67.1 |
| 5,765,875 A | 6/1998 | Rowley | ............... | 283/74 |
| 5,775,919 A * | 7/1998 | Gardner | ............... | 434/408 |
| 5,833,330 A | 11/1998 | Kos | ............... | 312/209 |
| 6,089,974 A | 7/2000 | Ahmad | ............... | 462/55 |
| 6,150,942 A | 11/2000 | O'Brien | ............... | 340/573.1 |
| 6,179,509 B1 | 1/2001 | Suits | ............... | 402/79 |
| 6,205,693 B1 * | 3/2001 | Pliler et al. | ............... | 40/776 |
| 6,454,705 B1 | 9/2002 | Cosentino et al. | ............... | 600/300 |
| D477,842 S | 7/2003 | Morris | ............... | D19/26 |
| 6,659,675 B2 * | 12/2003 | Rew | ............... | 402/17 |

(Continued)

*Primary Examiner* — Lesley D Morris
*Assistant Examiner* — Shin Kim
(74) *Attorney, Agent, or Firm* — Sara C. Kanos; Nexsen Pruet, LLC (57) ABSTRACT

A system for alerting medical emergency personnel to a medical history of a patient. The system has a primary identifier suitable for attachment near an entrance to a building. The primary identifier has an indicia noting that a tri-fold portfolio is present. A secondary identifier is provided suitable for placement in the building wherein the secondary identifier has the indicia and a location of the tri-fold portfolio. The tri-fold portfolio has an outer portion with a top front cover and a bottom front cover with a back hingedly attached there between. Cascading file folders are attached to an interior of the back wherein when the top front cover and the bottom front cover are folded the cascading file folders are covered.

17 Claims, 8 Drawing Sheets

U.S. PATENT DOCUMENTS

| | | | |
|---|---|---|---|
| 6,767,215 B2 * | 7/2004 | Robertson | 434/432 |
| 6,824,052 B2 | 11/2004 | Walsh | 235/380 |
| 7,040,899 B2 * | 5/2006 | Armstrong | 434/430 |
| D620,052 S * | 7/2010 | Blue et al. | D20/18 |
| 7,886,465 B2 * | 2/2011 | Virvo | 40/539 |
| 2001/0045037 A1 * | 11/2001 | Bank et al. | 40/621 |
| 2003/0205489 A1 * | 11/2003 | Shumake et al. | 206/224 |
| 2006/0015368 A1 | 1/2006 | Hockey | 705/2 |
| 2006/0100909 A1 | 5/2006 | Climp et al. | 705/3 |
| 2006/0111941 A1 | 5/2006 | Blom | 705/2 |
| 2006/0168864 A1 * | 8/2006 | Chan | 40/733 |
| 2006/0229918 A1 | 10/2006 | Fotsch et al. | 705/3 |
| 2007/0074043 A1 | 3/2007 | Lacey | 713/186 |
| 2007/0083393 A1 | 4/2007 | Howell | 705/3 |
| 2007/0192142 A1 | 8/2007 | Nicholson et al. | 705/3 |
| 2008/0243545 A1 | 10/2008 | D'Ambrosia et al. | 705/2 |
| 2008/0255625 A1 | 10/2008 | Powers | 607/5 |
| 2008/0287746 A1 | 11/2008 | Reisman | 600/300 |
| 2009/0024416 A1 | 1/2009 | McLaughlin et al. | 705/3 |
| 2009/0037224 A1 | 2/2009 | Raduchel | 705/3 |

* cited by examiner

MINUTES COUNT
HEART ATTACK WARNING SIGNS

☐ CHEST PAIN MAY BE CONSTANT OR MAY COME AND GO WITH INCREASING INTENSITY. THE PAIN MAY BE DESCRIBED AS CRUSHING, SQUEEZING, UNRELIEVED INDIGESTION, OR UNCOMFORTABLE PRESSURE. FREQUENTLY DESCRIBED AS "THERE IS AN ELEPHANT ON MY CHEST."

☐ RADIATES PAIN MAY RADIATE TO THE NECK, JAW, BACK, SHOULDER AREA OR IN ONE OR BOTH ARMS.

☐ BREATHING DIFFICULTY SHORTNESS OF BREATH MAY BE PRESENT WITH OR WITHOUT CHEST PAIN.

☐ OTHER SIGNS MAY OR MAY NOT BE PRESENT: FAINTING (LOSS OF CONSCIOUSNESS), NAUSEA, VOMITING, SWEATING AND DIZZINESS.

IF YOU HAVE SOME OR ALL OF THESE SYMPTOMS call 9-1-1 FOR HELP. IF YOU CAN'T ACCESS EMERGENCY MEDICAL SERVICES (EMS), HAVE SOMEONE DRIVE YOU TO THE NEAREST HOSPITAL OR MEDICAL FACILITY. DO NOT DRIVE YOURSELF.

REMEMBER, IF YOU ARE HAVING A HEART ATTACK...
  MINUTES COUNT

Fig.5

LESS THAN 3
STROKE WARNING SIGNS

- ☐ FEELING LOSS OF FEELING OR MOVEMENT TO ONE SIDE OF BODY.

- ☐ VISION PARTIAL OR COMPLETE LOSS OF VISION. DOUBLE VISION MAY OCCUR.

- ☐ WALK UNABLE TO WALK NORMALLY, SHUFFLES OR DRAGS ONE LEG OR FOOT.

- ☐ FALLS INCREASED NUMBER OF FALLS, NEW BALANCE PROBLEMS.

- ☐ SPEECH IS ABSENT, SLURRED, OR CAN'T BE UNDERSTOOD.

- ☐ THOUGHTS JUMBLED, PROBLEMS THINKING, CAN'T SAY THE RIGHT WORDS, OR DOESN'T RECOGNIZE FAMILIAR PEOPLE.

- ☐ PAIN OR HEADACHE. CAN BE DESCRIBED AS "WORSE HEADACHE OR MY LIFE."

NOTE THE TIME THAT SYMPTOMS STARTED. WHEN A PERSON IS HAVING A STROKE CAUSED BY A BLOOD CLOT, "CLOT-BUSTER" MEDICATIONS NEED TO BE GIVEN WITHIN 3 HOURS OF THE START OF SYMPTOMS TO POSSIBLY PREVENT LASTING PARALYSIS OR OTHER DEFICITS FROM BECOMING PERMANENT. IF THE STROKE IS CAUSED BY BLEEDING IN THE BRAIN THE "CLOT-BUSTER" MEDICATIONS PROVIDE NO BENEFIT.

CALL 9-1-1 FOR EMERGENCY MEDICAL SERVICES...
REMEMBER YOU HAVE LESS THAN 3 HOURS.

MEDICAL MANAGER

CROSS-REFERENCE TO RELATED APPLICATIONS

The present application claims priority to pending U.S. Provisional Patent Application No. 61/168,136 filed Apr. 9, 2009 which is incorporated by reference.

BACKGROUND OF THE INVENTION

The present invention is related to a system for rapidly alerting medical professionals of the medical history of a patient in the event of an emergency. The present invention is also related to a method of alerting emergency personnel of pertinent medical facts related to a patient.

In a crisis or emergency situation the patient, family or friends are often unable to provide essential information to the paramedics in a quick accurate and precise manner. The patient may not be able to communicate, may be in intense pain, may have difficulty breathing and is often traumatized to the extent that they are unable to answer the vital questions necessary to aid in their immediate care or answer incorrectly.

The first minutes of a medical emergency are critical. When Emergency Medical Services (EMS) personnel arrive at the scene valuable time can be lost gathering information about the patient, medications being taken, health history, and even why they were called to the scene. Often the people at the scene are not aware of the medical history of the patient, the patient may be alone or the patient may be unconscious.

In an emergency situation the patient may be transported to an unfamiliar hospital where they are treated by doctors that are not familiar with them or their problems/history. Emergency medicine has evolved from the family doctor meeting you in the Emergency Room, to not even admitting patients at the hospital. Not only may the patient have an MD that is unfamiliar with the medical history of the patient but an unfamiliar nurse practitioner may be seeking to obtain a medical history from a patient who is unable to provide adequate answers.

It is required by The Joint Commission, Medicare, and the hospital to have a dictated history and physical of the patient by every doctor that is called in to see the patient on consult. These records are available from the hospital medical records department along with other medical records by just providing a signed release of information form. Unfortunately, the location of these records may not be known.

There has been a long standing need for a system of alerting emergency personnel to critical medical conditions of the patient. There has also been a long standing need for a method of alerting emergency personnel to critical medical conditions of a patient.

SUMMARY OF THE INVENTION

It is an object of the invention to provide a system for alerting medical emergency personnel to the medical conditions of a patient.

It is another object of the invention to provide a method of alerting medical emergency personnel to the medical conditions of a patient.

A particular feature of the invention is the ability to utilize the system, or method, without special training.

These and other advantages, as will be realized, are provided in a system for alerting medical emergency personnel to a medical history of a patient. The system has a primary identifier suitable for attachment near an entrance to a building. The primary identifier has an indicia noting that a tri-fold portfolio is present. A secondary identifier is provided suitable for placement in the building wherein the secondary identifier has the indicia and a location of the tri-fold portfolio. The tri-fold portfolio has an outer portion with a top front cover and a bottom front cover with a back hingedly attached there between. Cascading file folders are attached to an interior of the back wherein when the top front cover and the bottom front cover are folded the cascading file folders are covered.

Yet another embodiment is provided in a method for alerting medical emergency personnel of a medical condition of a patient in a building. The method includes the steps of:
providing a tri-fold portfolio wherein the tri-fold portfolio has:
an outer portion with a top front cover, and bottom front cover with a back hingedly attached there between; and
cascading file folders attached to an interior of the back wherein when the top front cover and the bottom front cover are folded the cascading file folders are covered;
entering medical information on the tri-fold portfolio wherein the medical information indicates a presence of detailed medical records stored in the cascading file folders;
entering the detailed medical records in the cascading file folders;
attaching a primary identifier to the building near an entrance;
attaching a secondary identifier to a visible location in the building wherein the secondary identifier comprises a location of the tri-fold portfolio;
reviewing the primary identifier when entering the building;
searching for the secondary identifier and reviewing the location contained thereon; and
locating the tri-fold portfolio containing the medical information.

DETAILED DESCRIPTION

The present invention is directed to a system, and method. For alerting emergency personnel to the medical condition of a patient. More specifically, the present invention is related to a medical management system, and system of use, which greatly expedites alerting emergency personnel to the medical condition of a patient.

The invention will be described with reference to the various figures which form an integral, non-limiting, part of the instant application. Throughout the various figures similar elements will be numbered accordingly.

Figure 1:
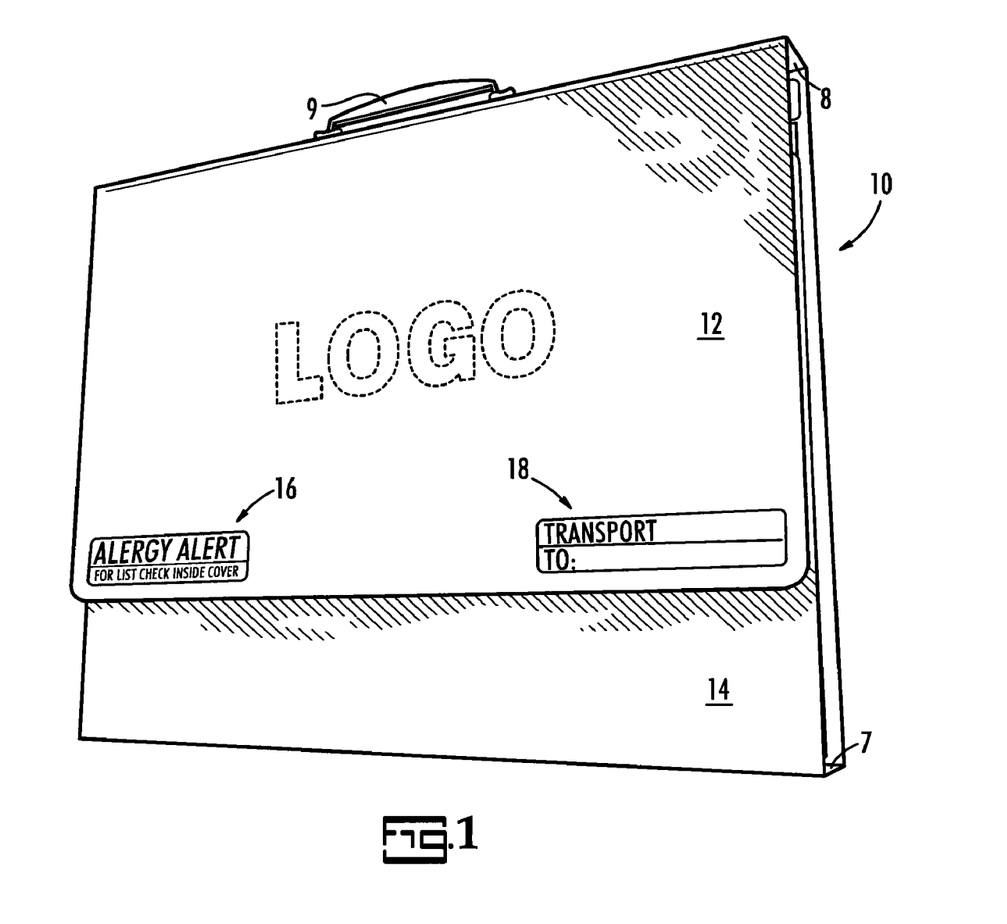
FIG. 1 is a front perspective schematic view of a closed tri-fold portfolio of the invention.
Figure 2:
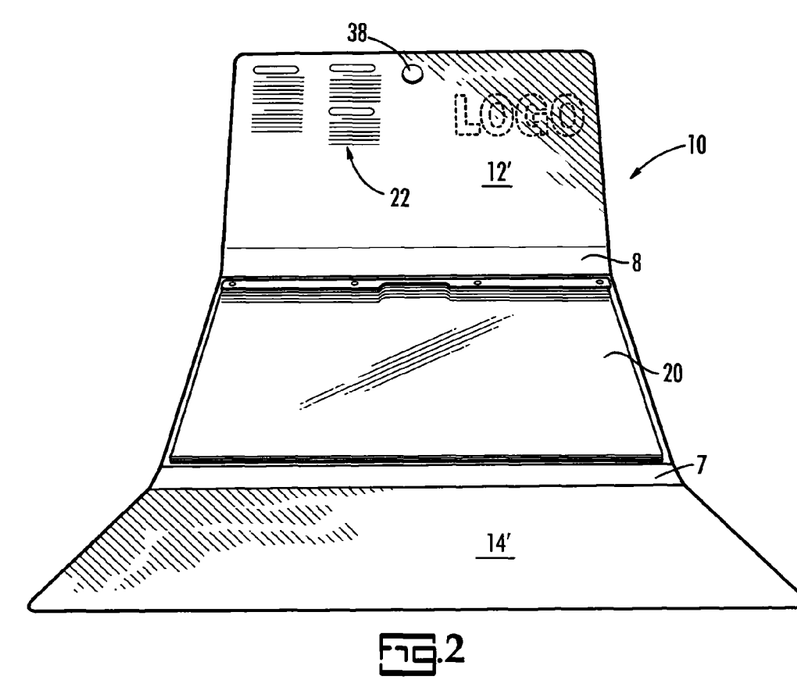
FIG. 2 is a front perspective schematic view of an open tri-fold portfolio of the invention.
Figure 3:
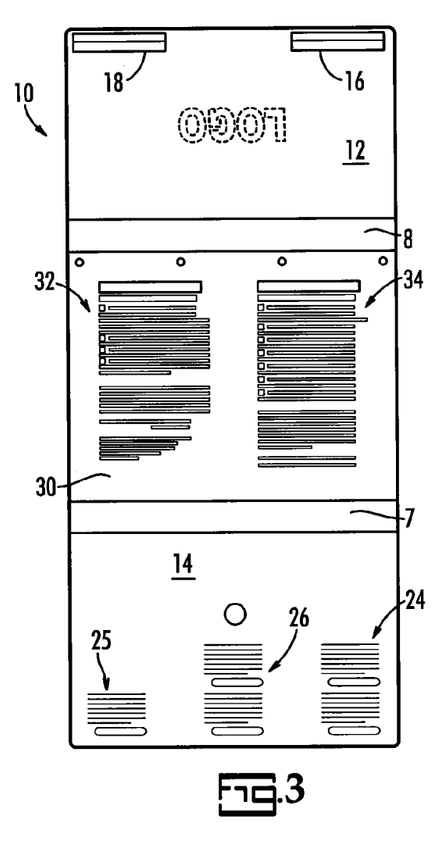
FIG. 3 is a rear schematic view of an open tri-fold portfolio of the invention.
Figure 4:
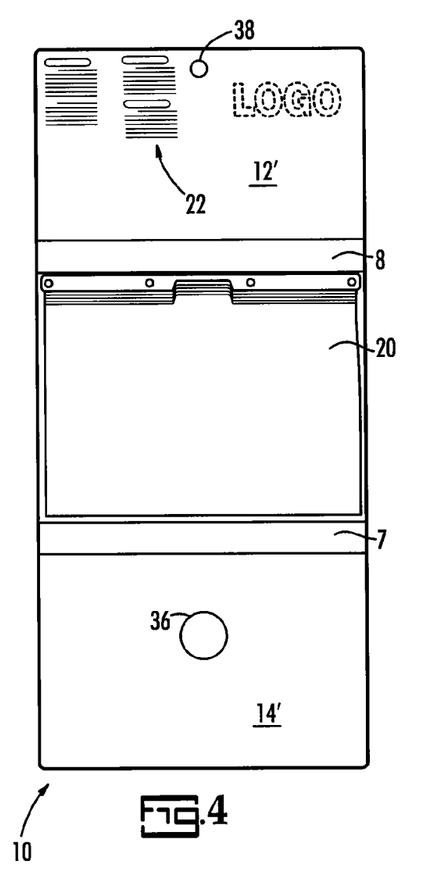
FIG. 4 is a front schematic view of an open tri-fold portfolio of the invention.

An embodiment of the invention will be described with reference to FIGS. 1-4. FIG. 1 is a perspective view of a tri-fold portfolio of the invention, when closed, and FIG. 2 is a perspective view of the tri-fold portfolio when opened. FIG. 3 illustrates the back side of the tri-fold portfolio and FIG. 4 illustrates the inside of the tri-fold portfolio. The inventive medical manager comprises a tri-fold portfolio, 10, comprising cascading file folders, 20, therein. The tri-fold portfolio, 10, comprises a top front cover, 12, and a bottom front cover, 14, each hingedly attached to either side of the back, preferably, at a spline. When closed the outer portion of the top front cover is visible and when open the inner portion, 12', of the top front cover is visible. The outer portion of the top front cover has an allergy alert logo, 16, alerting the user of the location within the folder for any information related to a patient allergy. A transport logo, 18, alerts the user of specific transport locations such as a local preferred hospital.

The inner portion of the top front cover comprises a logo, 22, listing disabilities such as blindness, hearing impairment, the use of a walker, the use of a cane, wheelchair dependence, dentures, past surguries, and immunizations such as tetanus, pneumonia, flu and hepatitis.

The outer portion of the bottom front cover comprises logos, 24, 26 and 28, comprising patient information related to the presence of medical history or conditions such as asthma, the use of blood thinners, the presence or propensity for blood clots, the presence and type of cancer, chronic obstructive pulmonary disorder (COPD), emphysema, chronic bronchitis, cardiac diseases such as previous heart attack, previous coronary by-pass surgery, the presence of cardiac stents or the presence of a pace maker or defibrillator, other heart problems, diabetes, hepatitis, pancreatitis, human immunodeficiency virus (HIV), orthopedic issues, psychiatric or mental health issues, renal issues such as dialysis dependence, past strokes, other problems and allergies. The bottom front cover printed areas are preferably 3.75 inches (96 mm) wide by 7.0 inches (178 mm) long.

Figure 5:
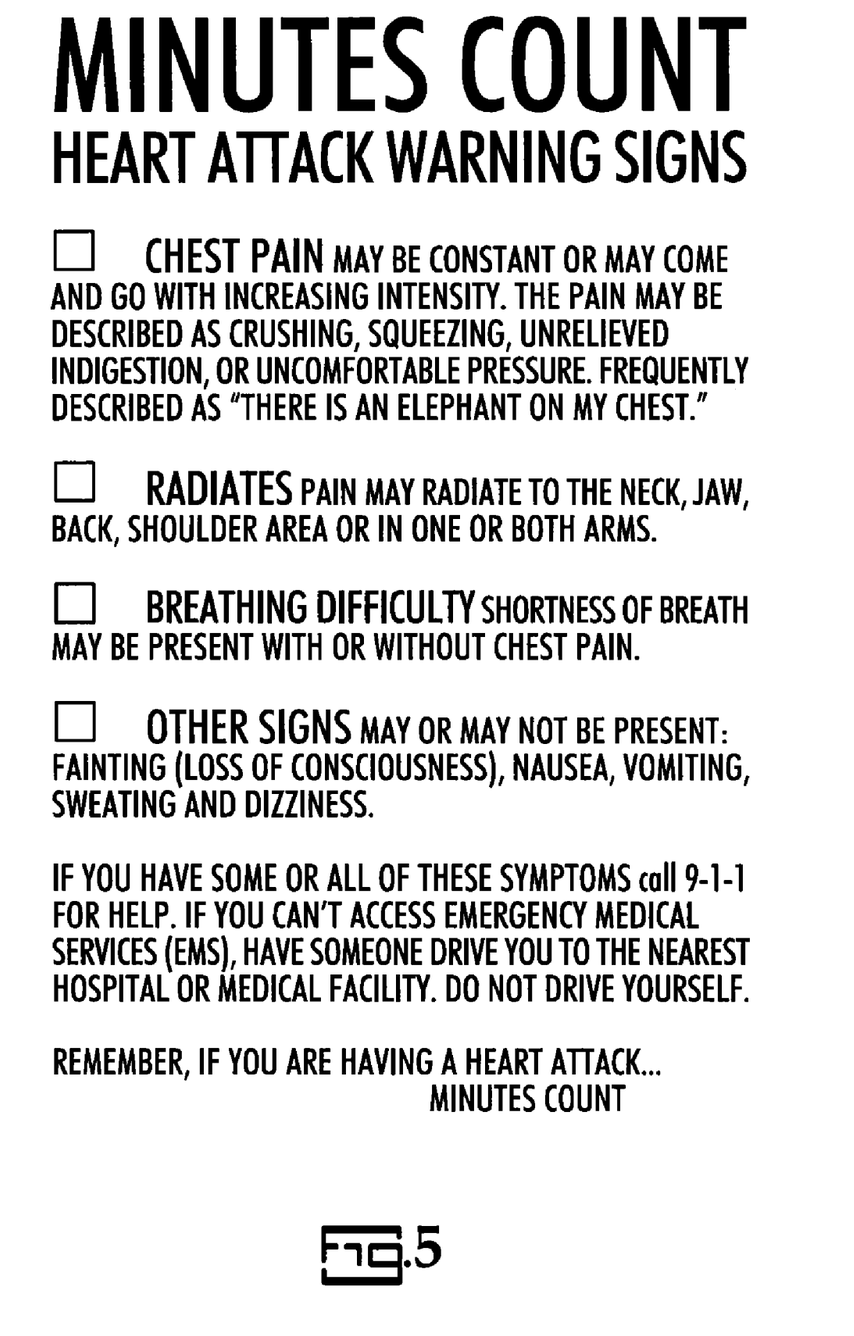
FIG. 5 is a graphical representation of a logo of the tri-fold portfolio.
Figure 6:
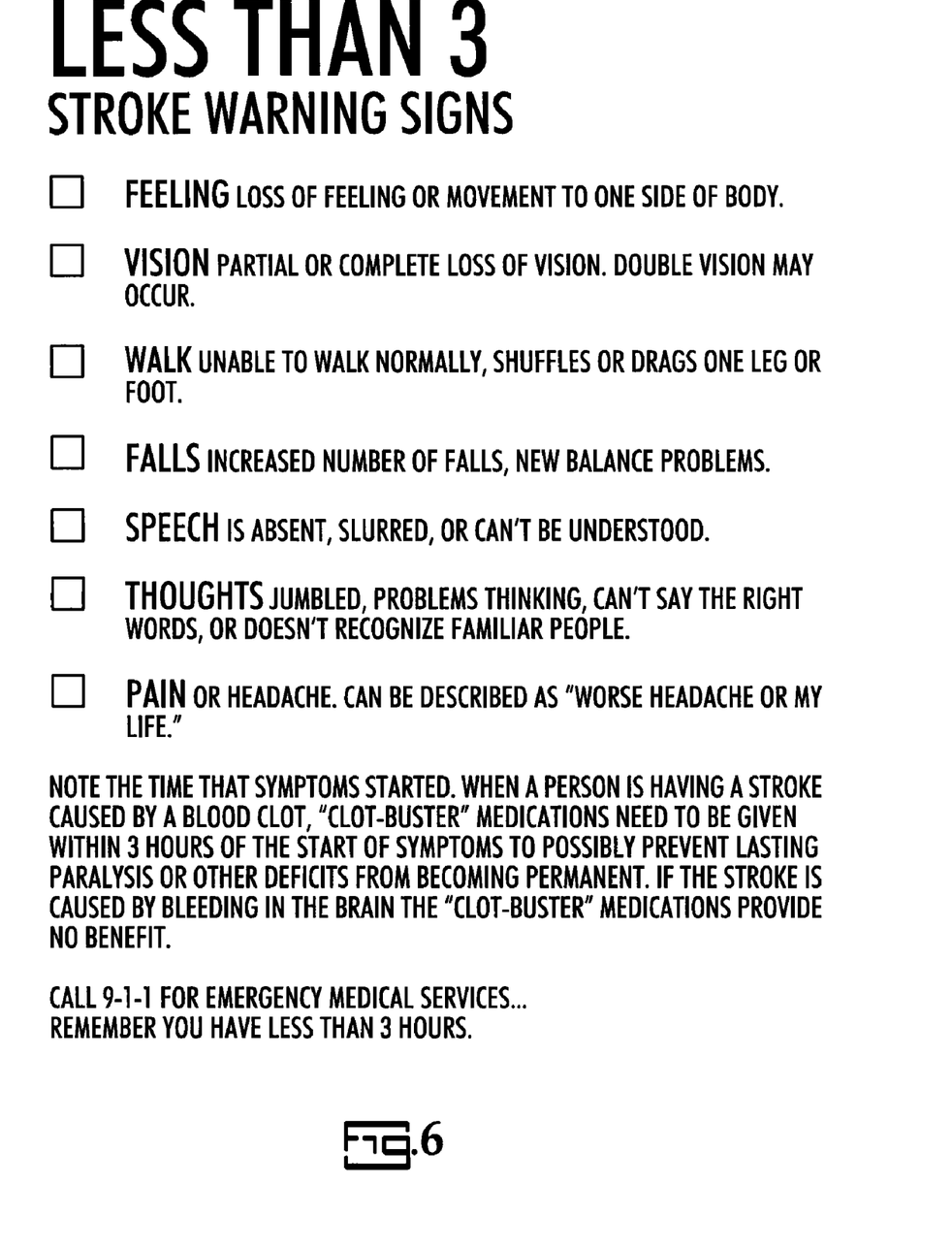
FIG. 6 is a graphical representation of a logo of the tri-fold portfolio.

The top front cover preferably has 2-3 areas of printing each approximately 2.5 inched by 3 inches. The back cover print area is preferably approximately 11.0 inches (279 mm) wide by about 8.5 inches (229. mm) long. The back, 30, of the tri-fold portfolio comprises a logo, 32, and a logo 34. Logo, 32, provides warnings related to heart attack symptoms as more specifically set forth in FIG. 5 and logo, 34, provides stroke warning signs as more specifically set forth in FIG. 6. The bottom left print area is preferably about 3.0 inches (76 mm) wide by about 3.0 inches (776 mm) long and the right side print area is preferably 3.0 inches (76 mm) wide by about 3.0 inch (76 mm) long.

The tri-fold portfolio is preferably a very good quality polypropylene (PP) with a solid matte finish. The closed size is preferably A4 letter size. It would be apparent that the PP needs to be printable during manufacturing. It is preferable that all corners are rounded and the creases and/or folded areas are to be pre-scored.

The color of the tri-fold portfolio is preferably completely orange with acridine orange 186 representing a particularly preferred color.

A first closure element, 36, attached to the inside bottom front cover, 14', mates with a second closure element, 38, to reversibly secure the tri-fold portfolio in a closed position. The mating closure elements can be a two piece magnetic closure with a vinyl semi-circle preferably of bright blue with the magnetic locking internalized. The closure is preferably securely attached by sewing or by small rivets. The closure is preferably the same color as the handle and is preferably located at the bottom center of the top flap. A preferred closure element is a hook and loop mechanism, such as Velcro®.

A handle, 9, is preferably on the upper spine, 8. A lower spine, 7 and upper spine, 8, hingedly connect the top front cover and bottom front cover to the back. The handle is preferably polypropylene and may be a different color than the tri-fold portfolio with bright blue, and particularly pantone PMS 300, being preferred. The handle is preferably securely attached to center top spine of case.

Figure 7:
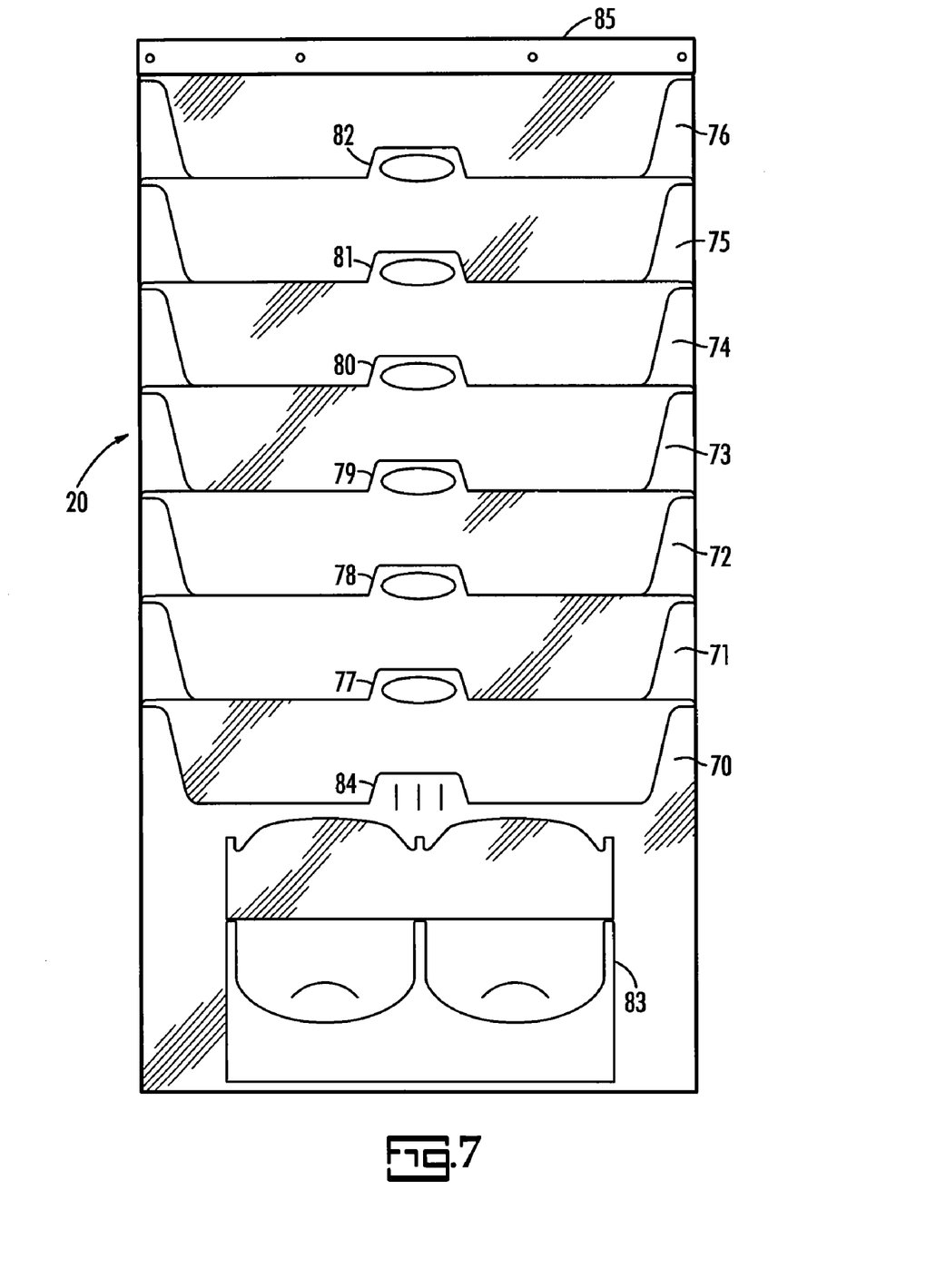
FIG. 7 is a schematic representation of cascade folders of the tri-fold portfolio.

The cascading file folders of the tri-fold portfolio will be described with particular reference to FIGS. 7-9. The file folders slide along each other to an open position as illustrated in FIG. 7. They can be collapsed such that the stack of folders is approximately the same length and width as a single folder. These are referred to as cascading folders. The first file folder, 70, differs from the remaining secondary file folders, 71-76, as will be described below. The secondary file folders, 71-76, are similar which each file folder being offset downward with distance from the back of the tri-fold portfolio when cascaded. Therefore, when the tri-fold portfolio is open, as in FIG. 4, the file folders can each be displaced in a cascading fashion. This allows the tabs, 77-82 to appear stacked and therefore more visible. The file folder which is furthest back in the cascading stack, 76, comprises an attachment tab, 85, for attaching the cascading file folders to the inside of the tri-fold portfolio on the inside opposite the back, 30 (see FIG. 3) of the tri-fold portfolio.

There are preferably seven or eight cascading files of heavy duty translucent velvet finish polymeric material. The file sizes are preferably 13.125 inches (333 mm) wide by 12.5 inches (328 mm) long. It is preferably that each file have a reinforcing strip of polymer that is heat stapled under each file's top fold. The files have an index tab at the center top which is 2.25 inches (57 mm) wide by 0.625 inches (15 mm) long with rounded corners. The tabs may have slanted edges on the left and right sides. The files cascade toward and over the bottom front inside flap when cascaded.

The first file folder is preferably shorter on the front edge than the secondary files by 2.50 inches (64 mm) with the same index tab used in center. The front of the first file folder comprises slide-in flat pouches, preferably at least 2, which are preferably heat stapled to the first file folder.

Figure 8:
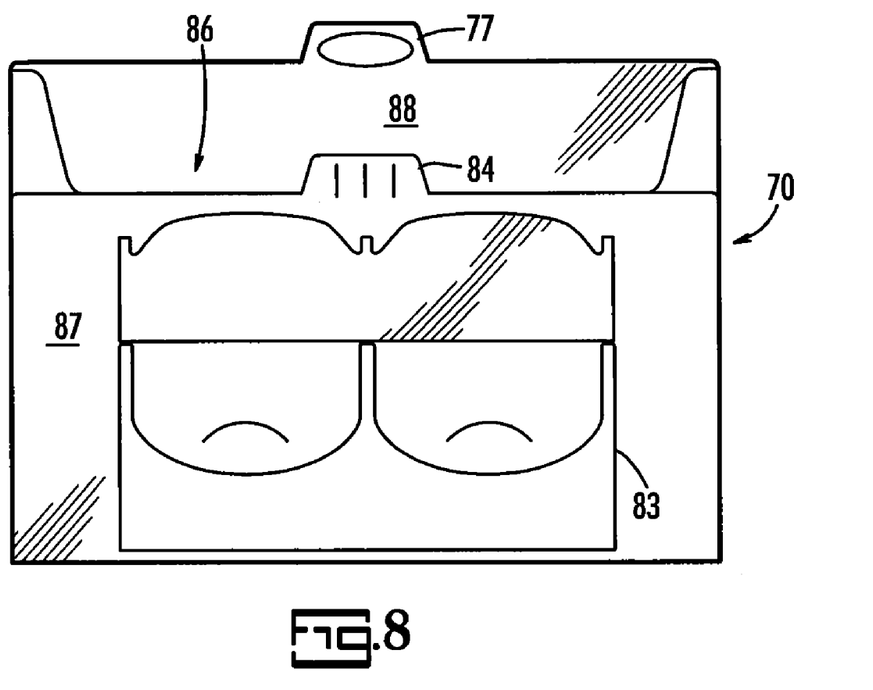
FIG. 8 is a schematic representation of a first folder of the tri-fold portfolio.
Figure 9:
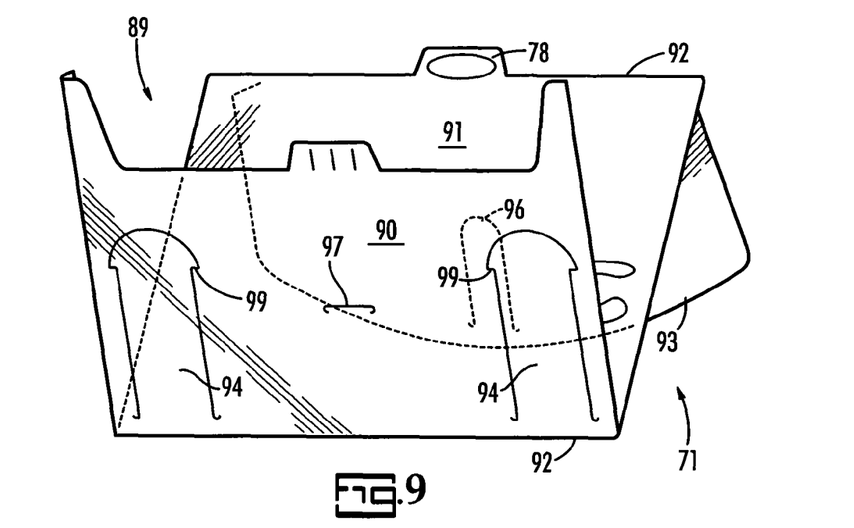
FIG. 9 is a schematic representation of secondary folders of the tri-fold portfolio.

The first file folder is illustrated in isolation in FIG. 8. In FIG. 8, the first file folder has a tab, 77, which allows the user to indicate the documents contained in the adjacent file folder. An exterior pouch, 83, or pocket, is provided on the exterior of the first file folder for containing at least one of an insurance card, an identification card or a compact disk with pertinent medical information contained in the tri-fold portfolio duplicated on the compact disk. The pouch size is preferably 5.25 inches (133 mm) wide by 6.0 inches (152 mm) long. This pouch preferably holds a CD. Pouches may be combined together for application on to file. The pouch corners are preferably rounded. It is preferable to have two closable pouches with a fastening slit, Velcro® closure, or snap closure over the slide in pouches. No longer will you have to sort through your wallet to find your insurance cards. The medical manager has a pouch for them as soon as the case is opened they will be plainly visible. A first folder tab, 84, describes the documents contained in the first folder. The file folder contains an interior portion, 86, bound by a front sheet, 87, and back sheet, 88, which are joined at the edges. Documents are placed in the interior portion. The first folder is preferably for do not resuscitate orders (DNR), living wills, and medical power of attorney.

The secondary file folders will be described with reference to FIG. 9 wherein the second file folder, 71, is illustrated as being representative of the other secondary file folders. Each file folder has an interior portion, 89, bound by a front sheet, 90, and back sheet, 91, which are joined at a hinge, 92. The tab, 78, is integral to the back sheet, 91, and extends upward there from. A rear leaf, 93, is attached to the back sheet, 91, at a hinge, 92. The rear leaf of one file folder is inserted into the interior portion of the adjacent folder thereby allowing the folders to slide relative to one another without substantial separation. The leaf comprises a finger, 96, which is received in a finger slot, 97, of an adjacent folder. At least one flap, 94, of each folder is slidably received in a slot, 99, of an adjacent folder. A protrusion, 98, forms a stop which limits the sliding distance of one folder relative to the adjacent folder. The combination of the leaf and the slidably received flap allow each adjacent folder to slide parallel to each other while the back of one folder and front of the adjacent folder remain in close proximity throughout the full range of cascading. As discussed above the most rearward secondary folder is attached to the tri-fold portfolio.

Each secondary file folder receives a specific document, or set of related documents, which corresponds to the title on the tab. For example, the tab may refer to the critical care instructions and the secondary file folder may contain a medical power of attorney, a do not resuscitate order or the like. The tab may refer to contacts and the folder may contain a list of critical contacts such as person to contact in case of an emergency, the contact information for the primary care physician, the contact information for the medical specialist, etc. The tab may refer to the schedule of medication and the document in the folder may contain a listing of medications and doses. The tab may refer to insurance and the folder may include additional information related to insurance such as copayment information, network information, life insurance information and the like. The tab may refer to forms and the folder may contain medical release forms. Many people have addressed end of life issues by having healthcare power of attorney (POA), do not resuscitate (DNR), or living wills. They don't have any way of letting EMS know where these things are kept and their families may not know where to look for them. The medical manager makes the important papers accessible. Preferred tabs are medications, doctors, history and physical, labs, EKGs and scans with the documents represented by each tab stored behind the tab.

The first folder is preferably for personal information and the documents in the first folder are preferably a picture to assist in identifying the individual and general information such as date of birth, blood type, social security number, dental records for identification purposes, physical address and the like.

Each file folder preferably has a width of 13.5 inches (343 mm), a height of 10.5 inches (267 mm) and a depth of 1.25 inches (32 mm). The open length of the tri-fold portfolio is preferably 31.0 inches (787 mm). The front top flap is preferably 13.5 inches (343 mm) wide by 8.0 inches long (203 mm). The front bottom flap is preferably 13.5 inches (343 mm) wide by 9.0 inches (229 mm) long. The back outside is preferably 13.5 inches (343 mm) wide by 10.5 inches (267 mm) long. The top and bottom spines are preferably 13.5 inches (343 mm) wide by 1.25 inches (32 mm).

The medical manager may be assembled by the patient/ family at their leisure based on instructions provided therein. All of the information is more easily obtained by the patient in a non stressful time and environment prior to an emergency.

The medical manager has a place for requesting a medical history from the patient's doctor that can be placed in the medical manager.

Figure 10:
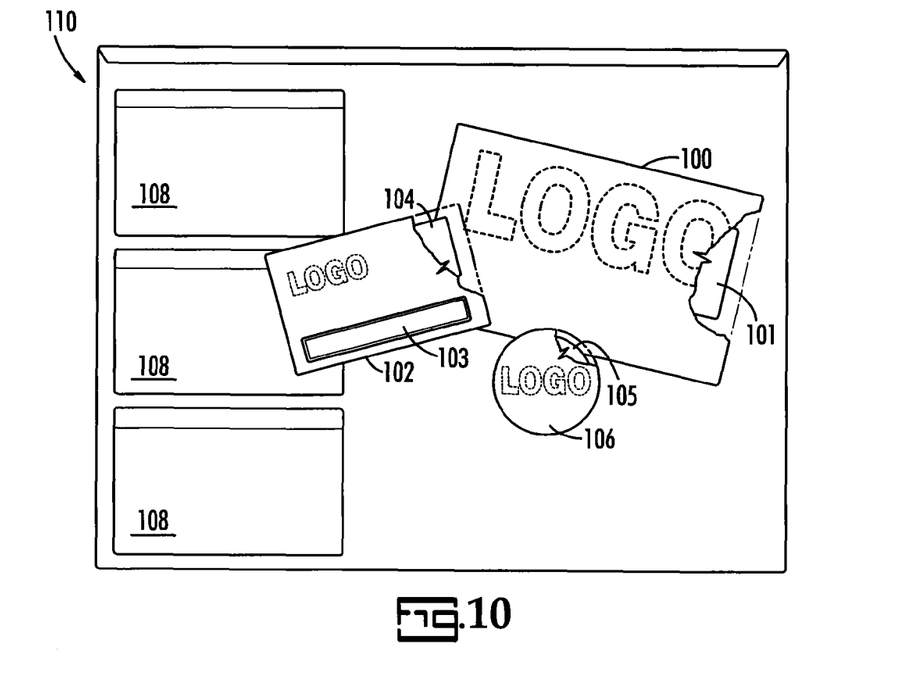
FIG. 10 is a schematic cut-away representation of the additional elements of the system of the invention.

In an embodiment of the invention the medical manager comprises a system comprising the tri-fold portfolio described above with identifiers. Identifiers are illustrated in FIG. 10. In FIG. 10, at least one primary identifier, 100, is provided which is relatively large and placed at, or near, the entrance to a house. Preferred locations include the front door or a window near the front door. A second primary identifier can be placed at an alternate entrance such as a side door, rear door, etc. The purpose of the primary identifier is to alert medical personnel that a tri-fold portfolio is available in the residence. The primary identifier, 100, preferably comprises a logo on the front indicative of the medical management system. An attachment element, 101, such as a magnet or adhesive is provided on the back of the primary identifier. The attachment element allows the primary identifier to be attached at, or near, the entrance.

A secondary identifier, 102, is similar to the primary identifier with the exception of a user field, 103, wherein the patient prints the location of the tri-fold portfolio. The user may state dresser, front closet, kitchen cabinet, bathroom closet, etc. to indicate the location of the tri-fold portfolio. The secondary identifier comprises an attachment element, 104, such as a magnet or adhesive which allows the secondary identifier to be attached. It is most preferred that the secondary identifier be attached to a refrigerator or another conspicuous location to insure that the emergency personnel can locate the secondary identifier with minimal searching.

A final identifier, 106, is preferably smaller than the primary or secondary identifier and is placed on the exterior of the location containing the tri-fold portfolio. The final identifier comprises the familiar logo on the front and an attachment element, 105, on the back which can be an adhesive or a magnet. An adhesive is preferred for the final identifier since it is most likely to be placed on a drawer. A card holder, 110, which is preferably a free sheet, allows for storage of business cards of doctors and the like. A multiplicity is provided with nine per sheet being most preferred.

Each identifier preferably has a consistent logo thereby insuring that medical personnel can visually identify the presence of a portfolio, based on a visual observation of the primary identifier; determine the location, based on the information contained on the secondary identifier; and then locate the tri-fold portfolio by visually becoming aware of the final identifier. There may be multiple secondary identifiers with each containing the same information in the user field. It is most preferred that there only be one final identifier.

The first place that the identifier will be displayed is on the front door of the user's home or on a window next to the front door. The identifier preferably has colors that are outlined in bright blue with yellow arms, white gloves, blue legs and feet and a blue bow tie. Lettering is preferably dark blue with orange showing through or solid dark bright blue. It is preferred to use highly visible colors that are easily spotted at the residence. The medical manager file case is preferably bright orange so it is easily spotted where ever it is kept.

The identifier on the door will denote to EMS that the medical manager tri-fold portfolio system is being used at the home. The medical manager can be kept by the entrance for easy access by EMS in time of an emergency. Also, on the refrigerator will be a secondary identifier this one will have a space that the user writes in the location that the medical manager tri-fold portfolio is kept. This will come into play if it is not easily spotted or out in the open. If the medical manager tri-fold portfolio is kept in a drawer or in a cabinet this will be disclosed at this location. A small dime or quarter sized final identifier is preferably provided that can be applied to the drawer or cabinet that is housing the medical manager tri-fold portfolio.

By using the inventive system the time that is taken to locate the vital information will be minimized.

The invention is preferable over electronic methods since the EMS is often unable to use an electronic method due to uncertainties that the software is virus free and compatible with their computer systems.

The medical manager tri-fold portfolio is designed to give EMS a quick glance into the patient's medical picture within 30 seconds. Medical history is displayed on the inside front cover. With a short composite list of major ailments that many in the population have. The medical manager is a safety measure that can save the life of the patient if it is used properly.

Many drugs can not be used if the patient is taking a medication which is not compatible. There is also the possibility that the patient is allergic to certain medications. Part of the medical history provided by the tri-fold portfolio is an allergy list. This list is to be filled in by the patient, prior to an emergency, so it is readily ascertainable if the patient has any allergies. If a patient receives medications that they are allergic to this can be a very harmful situation for them. Many times the family is unaware or unable to think fast enough to aid the EMT's.

Forms that will be needed to release information form to request records from the medical records department at the hospital. This form needs to be a multi-request form to get scan results, laboratory results, EKG's, surgical procedures note, etc. and will enable the patient to request multiple things with only one request form.

The medical manager is able to provide an instant medical history at a glance through its medical history section. A mark in the appropriate box next to the illness or condition that the patient suffers from gives EMS the medical history with just a quick glance. A complete history and physical section is supplied further in the med manager.

Due to the possibility of the medical manager getting exposed to water and moisture it is imperative that the ink in the marker not be water soluble, but the ink still needs to be changeable for the patient if something is marked in error or conditions change. It is preferable that the user be able to erase the marks with 70% isopropyl alcohol and not damage the printing on the folder.

The contact list will be one of the few hand written area that is in the medical manager. Many times the contact information provided includes home numbers or cell phone numbers only, and many of these have voice mail attached to them. A message may be left but not retrieved in a timely manner. The contact list herein preferably includes home addresses, place of employment and as much contact information as necessary.

It is preferable to provide multiple emergency contact numbers and multiple people. Many times people that accompany a patient to the ER do not have a list of phone numbers of people to contact. This has lessened some what with cell phones storing numbers but still can be a problem especially if the patient is not accompanied by a relative or close friend.

The system preferably includes sample DNR's healthcare POA's, living wills and related documents either in the tri-fold portfolio or available on associated website, available to purchasers, which are applicable for each state.

The inventive system is a label system keeps the medication list up to date and current at all times. By having a second label printed when you get a change of dosage, medication change you can replace the prior existing one in the file. Some cardiac medications, for example are used in treatment of psychiatric treatments. These patients may not have a heart history the inventive system provides sufficient information for a determination of which conditions are present by reading the labels.

The files are labeled for the most important parts of medical histories that we need to know up front. Strokes (CVA) and heart attacks are the #3 killer and the #1 killer in the US today therefore, warning signs of a heart attack and stroke are provided on the back of the tri-fold portfolio. This allows patients to readily view the signs and be familiar with them to possibly save their life due to rapid, and proper, intervention.

It is preferable to have a reinforcing strip applied on top of file attachment point on the inside back just below top spine which can be attached by small rivets.

The text can be screen printed or applied as labels preferably of a single color with the logo being either screen printed or an applied label with the logo being multi colored.

In some portions of the printed areas the patient will be required to write with either an ink pen or a medium point permanent marker. It is extremely important to the product that this ink/marker does not rub off or come off with water. Pen ink is to be able to be removed with 70% isopropyl alcohol and not damage the printed matter.

The invention has been described with reference to the preferred embodiments without limit thereto. One of skill in the art would readily realize additional embodiments and improvements which are not specifically listed but which are within the scope of the invention as more particularly set forth in the claims appended hereto.

The invention claimed is:

1. A system for alerting medical emergency personnel to a medical history of a patient comprising:
   a primary identifier suitable for attachment near an entrance to a building wherein said primary identifier comprises an indicia noting a tri-fold portfolio is present;
   a secondary identifier suitable for placement in said building wherein said secondary identifier comprises said indicia and a location of said tri-fold portfolio; and
   said tri-fold portfolio comprising:
   an outer portion with a top front cover, and bottom front cover with a back hingedly attached there between; and
   cascading file folders attached to an interior of said back wherein when said top front cover and said bottom front cover are folded said cascading file folders are covered, wherein said cascading folders comprise a first folder and at least one secondary folder, and wherein at least one secondary folder comprises an attachment tab.

2. The system for alerting medical emergency personnel to a medical history of a patient of claim 1 further comprising a final identifier.

3. The system for alerting medical emergency personnel to a medical history of a patient of claim 1 wherein said first folder comprises an exterior pouch.

4. The system for alerting medical emergency personnel to a medical history of a patient of claim 1 wherein each secondary folder comprises a tab.

5. The system for alerting medical emergency personnel to a medical history of a patient of claim 1 wherein at least one secondary folder comprises a rear leaf which is received in a flap of a second secondary folder.

6. The system for alerting medical emergency personnel to a medical history of a patient of claim 5 wherein said leaf comprises a finger received in a finger slot of said second secondary folder.

7. The system for alerting medical emergency personnel to a medical history of a patient of claim 1 wherein said tri-fold portfolio further comprises a handle.

8. A method for alerting medical emergency personnel of a medical condition of a patient in a building comprising:
   providing a tri-fold portfolio wherein said tri-fold portfolio comprises:
   an outer portion with a top front cover, and bottom front cover with a back hingedly attached there between; and
   cascading file folders attached to an interior of said back wherein when said top front cover and said bottom front cover are folded said cascading file folders are covered, wherein said cascading file folders comprise a first folder and at least one secondary folder, and wherein at least one secondary folder comprises an attachment tab;
   entering medical information on said tri-fold portfolio wherein said medical information indicates a presence of detailed medical records stored in said cascading file folders;
   entering said detailed medical records in said cascading file folders;
   attaching a primary identifier to said building near an entrance;
   attaching a secondary identifier to a visible location in said building wherein said secondary identifier comprises a location of said tri-fold portfolio;
   reviewing said primary identifier when entering said building;
   searching for said secondary identifier and reviewing said location contained thereon; and
   locating said tri-fold portfolio containing said medical information.

9. The method for alerting medical emergency personnel of a medical condition of a patient in a building of claim 8 further comprising a final identifier.

10. The method for alerting medical emergency personnel of a medical condition of a patient in a building of claim 8 wherein said first folder comprises an exterior pouch.

11. The method for alerting medical emergency personnel of a medical condition of a patient in a building of claim 8 wherein each secondary folder comprises a tab.

12. The method for alerting medical emergency personnel of a medical condition of a patient in a building of claim 8 wherein at least one secondary folder comprises a rear leaf which is received in a flap of a second secondary folder.

13. The method for alerting medical emergency personnel of a medical condition of a patient in a building of claim 8 wherein said tri-fold portfolio further comprise a handle.

14. A system for alerting medical emergency personnel to a medical history of a patient comprising:
   a primary identifier suitable for attachment near an entrance to a building wherein said primary identifier comprises an indicia noting a tri-fold portfolio is present;
   a secondary identifier suitable for placement in said building wherein said secondary identifier comprises said indicia and a location of said tri-fold portfolio; and
   said tri-fold portfolio comprising:
   an outer portion with a top front cover, and bottom front cover with a back hingedly attached there between; and
   cascading file folders attached to an interior of said back wherein when said top front cover and said bottom front cover are folded said cascading file folders are covered, wherein said cascading file folders comprise a first folder and at least one secondary folder, wherein at least one secondary folder comprises a rear leaf which is received in a flap of a second secondary folder, and wherein said leaf comprises a finger received in a finger slot of said second secondary folder.

15. A method for alerting medical emergency personnel of a medical condition of a patient in a building comprising:
   providing a tri-fold portfolio wherein said tri-fold portfolio comprises:
   an outer portion with a top front cover, and bottom front cover with a back hingedly attached there between; and
   cascading file folders attached to an interior of said back wherein when said top front cover and said bottom front cover are folded said cascading file folders are covered, wherein said cascading file folders comprise a first folder and at least one secondary folder, and wherein each secondary folder comprises a tab;
   entering medical information on said tri-fold portfolio wherein said medical information indicates a presence of detailed medical records stored in said cascading file folders;
   entering said detailed medical records in said cascading file folders;
   attaching a primary identifier to said building near an entrance;
   attaching a secondary identifier to a visible location in said building wherein said secondary identifier comprises a location of said tri-fold portfolio;
   reviewing said primary identifier when entering said building;
   searching for said secondary identifier and reviewing said location contained thereon; and
   locating said tri-fold portfolio containing said medical information.

16. A method for alerting medical emergency personnel of a medical condition of a patient in a building comprising:
   providing a tri-fold portfolio wherein said tri-fold portfolio comprises:
   an outer portion with a top front cover, and bottom front cover with a back hingedly attached there between; and
   cascading file folders attached to an interior of said back wherein when said top front cover and said bottom front cover are folded said cascading file folders are covered, wherein said cascading file folders comprise a first folder and at least one secondary folder, and wherein at least one secondary folder comprises a rear leaf which is received in a flap of a second secondary folder;
   entering medical information on said tri-fold portfolio wherein said medical information indicates a presence of detailed medical records stored in said cascading file folders;
   entering said detailed medical records in said cascading file folders;
   attaching a primary identifier to said building near an entrance;
   attaching a secondary identifier to a visible location in said building wherein said secondary identifier comprises a location of said tri-fold portfolio;
   reviewing said primary identifier when entering said building;
   searching for said secondary identifier and reviewing said location contained thereon; and
   locating said tri-fold portfolio containing said medical information.

17. A system for alerting medical emergency personnel to a medical history of a patient comprising:

a primary identifier suitable for attachment near an entrance to a building wherein said primary identifier comprises an indicia noting a tri-fold portfolio is present;

a secondary identifier suitable for placement in said building wherein said secondary identifier comprises said indicia and a location of said tri-fold portfolio; and said tri-fold portfolio comprising:

an outer portion with a top front cover, and bottom front cover with a back hingedly attached there between; and cascading file folders attached to an interior of said back wherein when said top front cover and said bottom front cover are folded said cascading file folders are covered, wherein at least one cascading folder comprises a flap on a front which is slidably received in a slot on a back of an adjacent folder, and wherein said flap comprises a protrusion to limit sliding of adjacent folders.

* * * * *